(12) United States Patent
Gupta et al.

(10) Patent No.: US 12,364,485 B2
(45) Date of Patent: Jul. 22, 2025

(54) ARTERIAL OCCLUSION IMPLANT AND DELIVERY CATHETER AND METHODS

(71) Applicants: Boston Scientific Scimed, Inc., Maple Grove, MN (US); Regents of the University of Minnesota, Minneapolis, MN (US)

(72) Inventors: Ajay Gupta, Minneapolis, MN (US); Enio Perez Torres, Minneapolis, MN (US); Joshua Dean Shafer, Minneapolis, MN (US); Camden Schneider Sundin, Minneapolis, MN (US); Samuel Benjamin Awes, Minneapolis, MN (US); Kenneth Patrick Urbanski, Minneapolis, MN (US)

(73) Assignees: BOSTON SCIENTIFIC SCIMED, INC., Maple Grove, MN (US); Regents of the University of Minnesota, Minneapolis, MN (US)

( * ) Notice: Subject to any disclaimer, the term of this patent is extended or adjusted under 35 U.S.C. 154(b) by 321 days.

(21) Appl. No.: 18/073,286

(22) Filed: Dec. 1, 2022

(65) Prior Publication Data
US 2023/0172615 A1 Jun. 8, 2023

Related U.S. Application Data

(60) Provisional application No. 63/285,544, filed on Dec. 3, 2021.

(51) Int. Cl.
*A61B 17/12* (2006.01)
*A61B 17/00* (2006.01)
(Continued)

(52) U.S. Cl.
CPC .. *A61B 17/12181* (2013.01); *A61B 17/12031* (2013.01); *A61B 17/1204* (2013.01);
(Continued)

(58) Field of Classification Search
CPC ........ A61B 17/12181; A61B 17/12031; A61B 17/1204; A61B 17/12109
See application file for complete search history.

(56) References Cited

U.S. PATENT DOCUMENTS 7,838,699 B2 11/2010 Schwarz et al.
8,241,311 B2 8/2012 Ward et al.
(Continued)

FOREIGN PATENT DOCUMENTS

JP 5341816 B2 11/2013

*Primary Examiner* — Sarah A Long
*Assistant Examiner* — Raihan R Khandker
(74) *Attorney, Agent, or Firm* — Seager, Tufte & Wickhem, LLP

(57) ABSTRACT

An artery can be occluded by implanting an occlusion implant within a subintimal space within a wall of the artery. As an example, a catheter having a side port just proximal of an inflatable balloon disposed near a distal end of the catheter can be advanced through the artery to a site at which an occlusion is desired. The inflatable balloon can be inflated and a guidewire can be advanced through a lumen of the catheter, out of the side port and into a subintimal space of the artery, with the inflated inflatable balloon guiding the guidewire towards the artery wall. An occlusion implant can be advanced over the guidewire into the subintimal space and the guidewire can be withdrawn, leaving the occlusion implant positioned within the subintimal space.

13 Claims, 13 Drawing Sheets

(51) Int. Cl.
*A61M 25/00* (2006.01)
*A61M 25/09* (2006.01)

(52) U.S. Cl.
CPC ... *A61B 17/12109* (2013.01); *A61M 25/0043* (2013.01); *A61M 25/09041* (2013.01); *A61B 2017/00004* (2013.01); *A61B 2017/00557* (2013.01); *A61B 2017/1205* (2013.01); *A61M 2025/09175* (2013.01)

(56) References Cited

U.S. PATENT DOCUMENTS

| | | |
|---|---|---|
| 10,327,791 B2 | 6/2019 | Morero et al. |
| 10,888,354 B2 | 1/2021 | Kugler et al. |
| 2010/0010339 A1 | 1/2010 | Smith et al. |
| 2012/0095485 A1* | 4/2012 | Cully ............... A61M 25/0054 606/159 |
| 2014/0018837 A1* | 1/2014 | Zhou ............... A61M 25/0194 606/194 |
| 2019/0134350 A1* | 5/2019 | Crisco ............... A61M 25/09 |
| 2025/0018104 A1* | 1/2025 | Rajendraprasad ................... A61B 17/3478 |

* cited by examiner

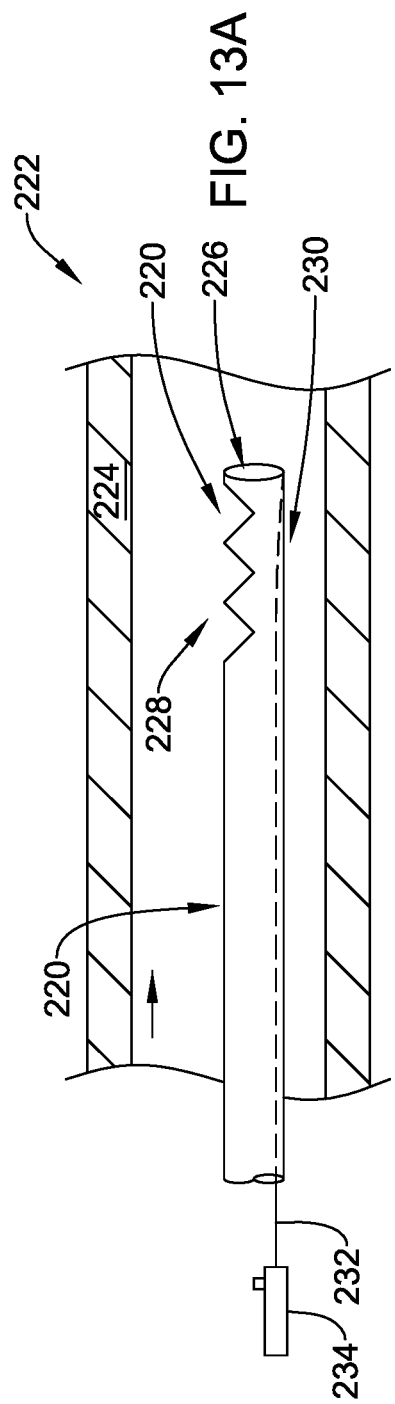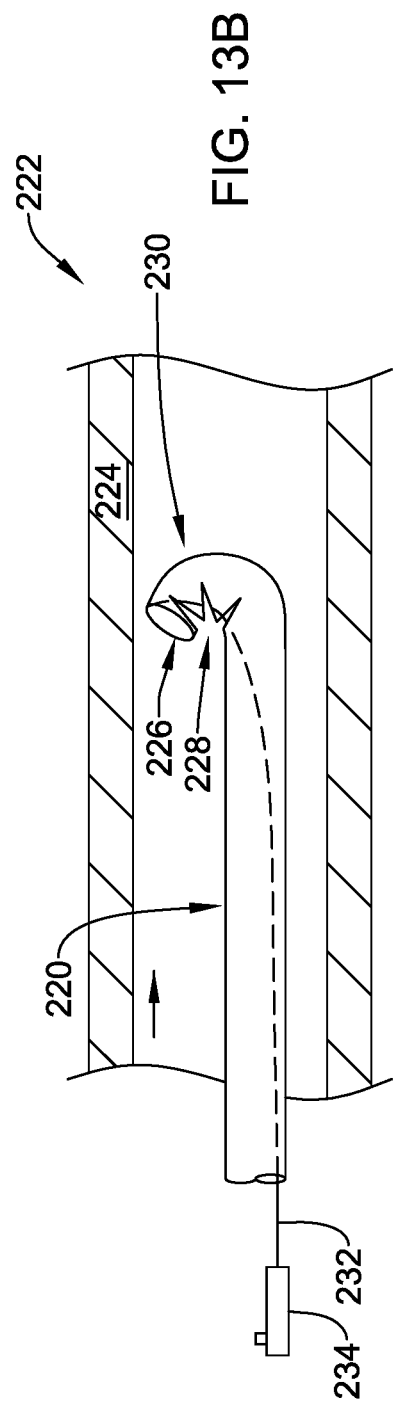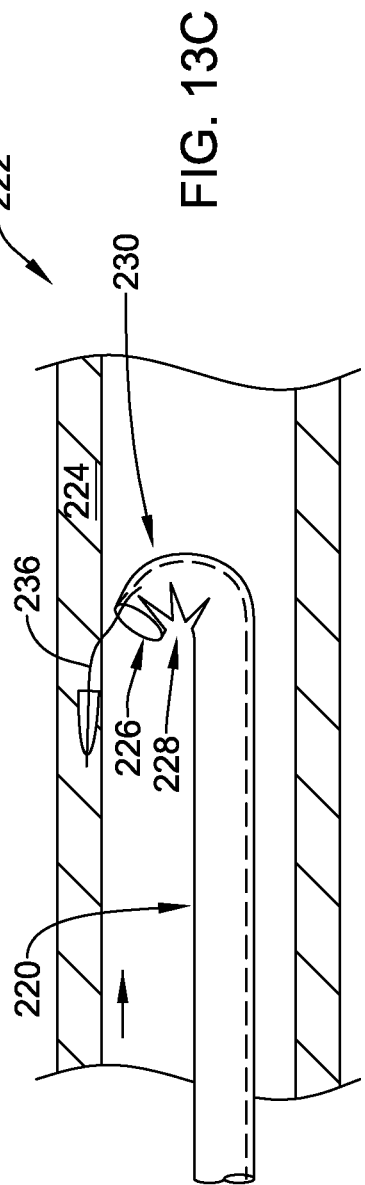

ARTERIAL OCCLUSION IMPLANT AND DELIVERY CATHETER AND METHODS

CROSS-REFERENCE TO RELATED APPLICATION

This application claims the benefit of priority under 35 U.S.C. § 119 of U.S. Provisional Application No. 63/285,544, filed Dec. 3, 2021, the entire disclosure of which is hereby incorporated by reference.

TECHNICAL FIELD

The present disclosure pertains to medical devices, and methods for manufacturing and using medical devices. More particularly, the disclosure is directed to an arterial occlusion implant and delivery thereof.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, a method of occluding an artery is disclosed. A catheter is advanced through the artery to a site at which an occlusion is desired, the catheter having a side port just proximal of an inflatable balloon disposed near a distal end of the catheter, and the inflatable balloon is inflated. A puncture guidewire is advanced through a lumen of the catheter, out of the side port and into a subintimal space of the artery, where the inflated inflatable balloon guides the puncture guidewire towards the artery wall. An occlusion implant is advanced over the puncture guidewire into the subintimal space. The puncture wire is withdrawn, leaving the occlusion implant positioned within the subintimal space.

Alternatively or additionally, the method may further include withdrawing the catheter from the artery, leaving the puncture guidewire in place, prior to advancing the occlusion implant over the puncture guidewire.

Alternatively or additionally, advancing the occlusion implant over the puncture guidewire may further include advancing a delivery catheter including the occlusion implant over the puncture guidewire.

Alternatively or additionally, the catheter may further include a central guidewire lumen, and advancing the catheter through the artery may include advancing a guide guidewire through the artery beyond the site at which the occlusion is desired, and advancing the catheter over the guide guidewire through the artery to the site at which the occlusion is desired.

Alternatively or additionally, the method may further include withdrawing the guide guidewire.

Alternatively or additionally, the occlusion implant may include a hydrophilic material.

Alternatively or additionally, the occlusion implant may include a biosorbable material.

Alternatively or additionally, the occlusion implant may include a rod-shaped profile and includes a lumen extending therethrough to allow the occlusion implant to be delivered over the puncture guidewire.

As another example, a method of occluding an artery is disclosed. A first guidewire is advanced through the artery beyond a site at which an occlusion is desired. A first catheter is advanced over the first guidewire to the artery to a site at which an occlusion is desired, the first catheter including a device lumen and an inflation lumen, the inflation lumen fluidly coupled with an inflatable balloon disposed on a first side of the catheter, the first catheter including a trap door on an opposing second side of the first catheter, the trap door providing access to the device lumen. The inflatable balloon is inflated, thereby pushing the second side of the first catheter towards a wall of the artery. The first guidewire is withdrawn, allowing the trap door to drop into the device lumen. A second guidewire is advanced out the trap door and into a subintimal space of the wall of the artery. A second catheter is advanced over the second guidewire through the trap door and into the subintimal space of the wall of the artery. The second guidewire is withdrawn. An occlusion implant is advanced through the second catheter into position within the subintimal space of the wall of the artery.

Alternatively or additionally, the first guidewire may include an atraumatic tip.

Alternatively or additionally, the second guidewire may include a tip adapted for piercing an intima of the artery wall.

Alternatively or additionally, the trap door may be hinged to a sidewall of the first catheter via a hinge disposed on a distal end of the trap door.

Alternatively or additionally, advancing an occlusion implant through the second catheter into position within the subintimal space of the wall of the artery may include using an elongate member to push the occlusion implant through the second catheter.

Alternatively or additionally, the occlusion implant may be adapted to temporarily occlude the artery.

Alternatively or additionally, the occlusion implant may be adapted to permanently occlude the artery.

As another example, an assembly is adapted for delivering an occlusion implant to a subintimal space within an artery. The assembly includes a first catheter, a first guidewire having an atraumatic tip and a second guidewire having a tip adapted for piercing an intima of a wall of the artery. The first catheter includes an elongate shaft including a distal region, the distal region including a first side and an opposing second side, and an inflation lumen extending through the elongate shaft. An inflatable balloon is fluidly coupled with the inflation lumen, the inflatable balloon disposed on the first side of the distal region. A device lumen extends through the elongate shaft and a trap door is disposed within the second side of the distal region, the trap door adapted to pivot into the device lumen.

Alternatively or additionally, the assembly may further include a second catheter adapted to be advanced through the device lumen.

Alternatively or additionally, the assembly may further include an occlusion implant.

Alternatively or additionally, the occlusion implant may include a hydrophilic material.

Alternatively or additionally, the trap door may be hinged to a sidewall of the first catheter via a hinge disposed on a distal end of the trap door.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 13A through 13C are schematic views showing an illustrative catheter useful in implanting an occlusion implant.

Figure 1:
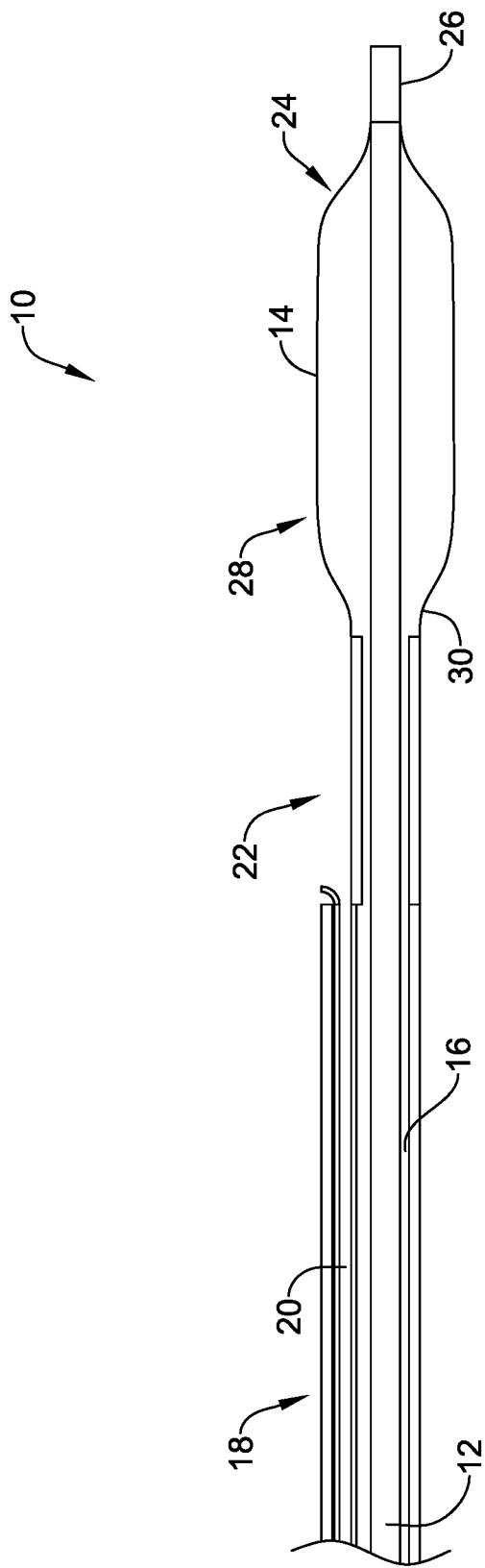
FIG. 1 is a schematic view of an illustrative catheter that is adapted for delivering an occlusion implant to a subintimal space within an artery wall.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Blood vessels such as arteries have vessel walls with multiple layers. The innermost layer is sometimes referred to as the endothelium. The area between the endothelium and other layers of the artery can be referred to as a subintimal space. Techniques for reaching the subintimal space, particularly for using the subintimal space to create a false lumen allowing passage past a completely occluded portion of an artery are known. Rather than trying to get around an existing occlusion, the disclosure pertains to using the subintimal space to implant an occlusion implant that will cause the artery in which the occlusion implant is implanted to be occluded.

There are a number of situations in which it may be desirable to reduce or even occlude blood flow through a particular artery, whether temporary or permanent. For example, there may be a desire to reduce blood flow to the spleen in order to treat conditions such as splenomegaly or thrombocytopenia. For gastro-intestinal bleeds, there may be a desire to reduce blood flow in order to allow an ulcer to heal. Bariatric artery embolization (for weight loss) is another example. Stopping bleeds in case of trauma is another example.

Gastric artery embolization before performing Y90 may prevent off-target delivery of radioactive particles is another example. Y90 refers to a radioembolization procedure in which tiny glass or resin beads filled with the radioactive isotope yttrium Y-90 are placed inside the blood vessels that feed a tumor.

Prostate artery embolization for reducing size of the prostate is another example. During prostate artery embolization, off-target embolization of rectal or penile arteries is a concern. *Geniculate* artery embolization to reduce pain is another example. Gradual constriction of blood flow to avoid harmful acute side effects is an advantage of temporarily occluding an artery, as is redirecting increased blood flow to an organ by constricting flow to other arterial branches.

FIG. 1 is a schematic view of an illustrative catheter 10 that may be used to reach the subintimal space of a particular artery as well as to implant an occlusion implant within the subintimal space. In some cases, the catheter 10 may be referred to as an OTW (over the wire) catheter, as the catheter 10 includes a central guidewire lumen 12 that can accommodate a guidewire such as a guide guidewire therethrough. As will be appreciated, the catheter 10 can be advanced over a guidewire (not shown) extending through the central guidewire lumen 12.

The catheter 10 includes an inflatable balloon 14. Accordingly, the catheter 10 includes an inflation lumen 16 that extends through an elongate shaft 18. The inflation lumen 16 extends proximally to a source of saline as inflation fluid (not shown), and extends distally such that the inflation lumen 16 is fluidly coupled with the inflatable balloon 14. Thus, saline that is pumped or otherwise provided through the inflation lumen 16 causes the inflatable balloon 14 to inflate. Conversely, withdrawing saline through the inflation lumen 16 causes the inflatable balloon 14 to deflate.

The catheter 10 includes a side lumen 20 that can be used to advance other members through the catheter 10, as will be discussed. For example, a guidewire such as a puncture guidewire (shown in FIG. 2) can be advanced through the side lumen 20. The occlusion implant itself (not shown in FIG. 1) can also be advanced through the side lumen 20, and in some cases may be advanced over the puncture guidewire itself. The side lumen 20 terminates at a side port 22 that is located just proximal of the inflatable balloon 14. The inflatable balloon 14 can be seen as including a distal taper 24 that tapers to a distal waist 26 and a proximal taper 28 that tapers to a proximal waist 30.

Figure 2:
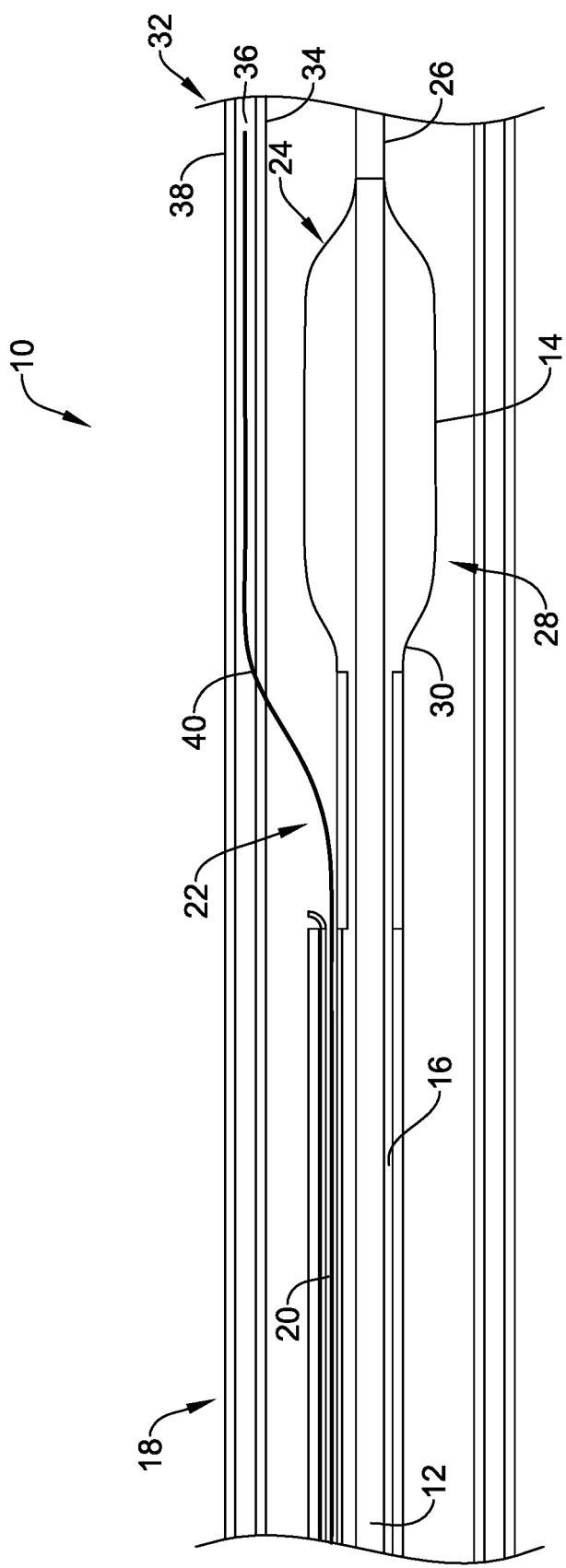
FIG. 2 is a schematic view of the illustrative catheter of FIG. 1, shown in position within an artery with a puncture guidewire extending through the illustrative catheter.

FIG. 2 is a schematic view of the catheter 10, disposed within an artery 32. The artery 32 is schematically shown as including an inner most layer or intima 34 that defines a subintimal space 36 between the intima 34 and one or more outer layers 38. It will be appreciated that this is merely illustrative, as the artery 32 has additional layers beyond those shown.

In some cases, inflating the inflatable balloon 14 may partially or even completely temporarily occlude the artery 32. This is temporary, and is done to assist with guiding a puncture guidewire 40 that has been advanced through the side lumen 20 and out the side port 22. In some cases, as shown, the tapered profile of the proximal taper 28 helps to guide the puncture guidewire 40 towards and even into the intima 34. After puncturing the intima 34, the puncture guidewire 40 can be seen as extending within the subintimal space 36. In some cases, extending the puncture guidewire 40 within the subintimal space 36 can serve to enlarge the subintimal space by helping to further separate the intima 34 from the outer layers 38. In some cases, the outer layers 38 are stronger than the intima 34, which can make it easier for the puncture guidewire 40 to penetrate through the intima 34 but not penetrate into the outer layers 38.

Figure 3:
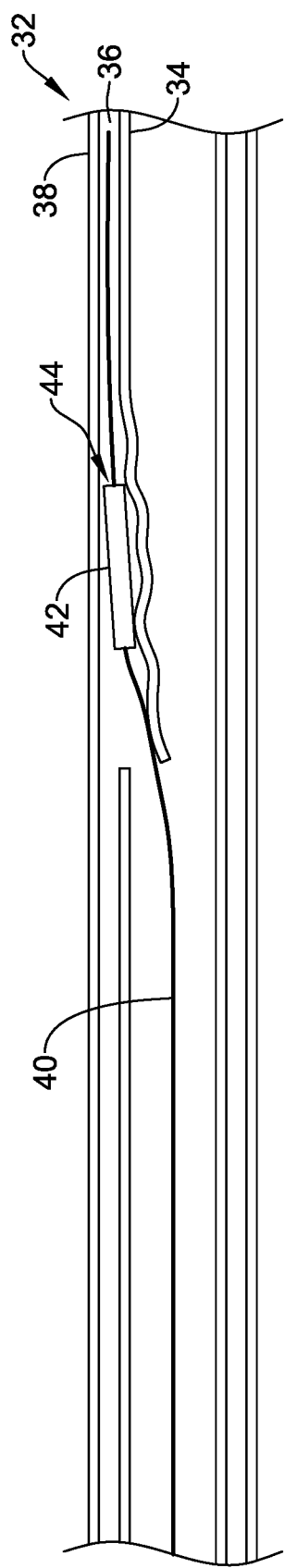
FIG. 3 is a schematic view of an illustrative occlusion implant disposed within the subintimal space of an artery wall.

In some cases, once the puncture guidewire 40 has reached the subintimal space 36 and has extended into the subintimal space 36, the inflatable balloon 14 can be deflated and the catheter 10 can be withdrawn. In FIG. 3, the catheter 10 has been withdrawn, leaving the puncture guidewire 40 extending through the artery 32 and into the subintimal space 36. An occlusion implant 42 has been advanced over the puncture guidewire 40 and into the subintimal space 36. As can be seen, the occlusion implant 42 includes a lumen 44 that extends through the occlusion implant 42, thereby allowing the occlusion implant 42 to be advanced over the puncture guidewire 40. Advancing the occlusion implant 42 into the subintimal space 36 can be seen as having further separated the intima 34 from the outer layers 38, thereby enlarging the subintimal space 36.

As shown, the occlusion implant 42 (as implanted) is rod-shaped. Other shapes are contemplated, although in some cases, the occlusion implant 42 will retain a minimal cross-sectional profile in order to facilitate implantation of the occlusion implant 42. While the occlusion implant 42 is shown here as being fully disposed within the subintimal space 36, in some cases it is contemplated that the occlusion implant 42 may be partially disposed within the subintimal space 36 and partially disposed outside of the subintimal space 36.

Figure 4:
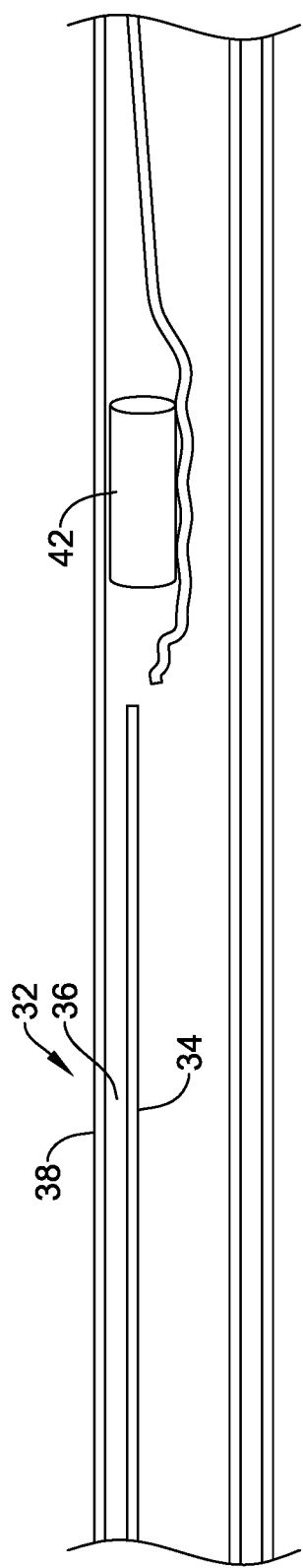
FIG. 4 is a schematic view of the illustrative occlusion implant of FIG. 3, after the illustrative occlusion implant has absorbed water and subsequently swelled.

In some cases, the occlusion implant 42 may be formed of a hydrophilic material that will absorb water from the blood plasma and will swell. FIG. 4 shows the occlusion implant 42 after the occlusion implant 42 has absorbed water and has enlarged in diameter, thereby further pushing the intima 34 across the artery 32 and closer to the outer layers 38. If the occlusion implant 42 swells sufficiently, the artery 32 will become completely occluded. The occlusion may be temporary or permanent, depending on what the occlusion implant 42 is made of. For example, if the occlusion implant 42 is made of a material that is bioabsorbable, the occlusion implant 42 will slowly break down over time, and will disappear. As the occlusion implant 42 disappears, the intima 34 will slowly return to its original position. It will be appreciated that any remaining blood flow through the artery 32 is largely in contact with the intima 34, allowing a smooth flow profile. Both of these factors reduce the changes of forming thrombus.

In some cases, the occlusion implant 42 may be formed of an absorbent scrunchy, that will expand once it absorbs fluids around the occlusion implant 42 after implantation. In some cases, the occlusion implant 42 may be a self-expanding stent, or a balloon-expandable stent, for example. The occlusion implant 42 may be an absorbent sponge that grows once it absorbs fluid.

Figure 5:
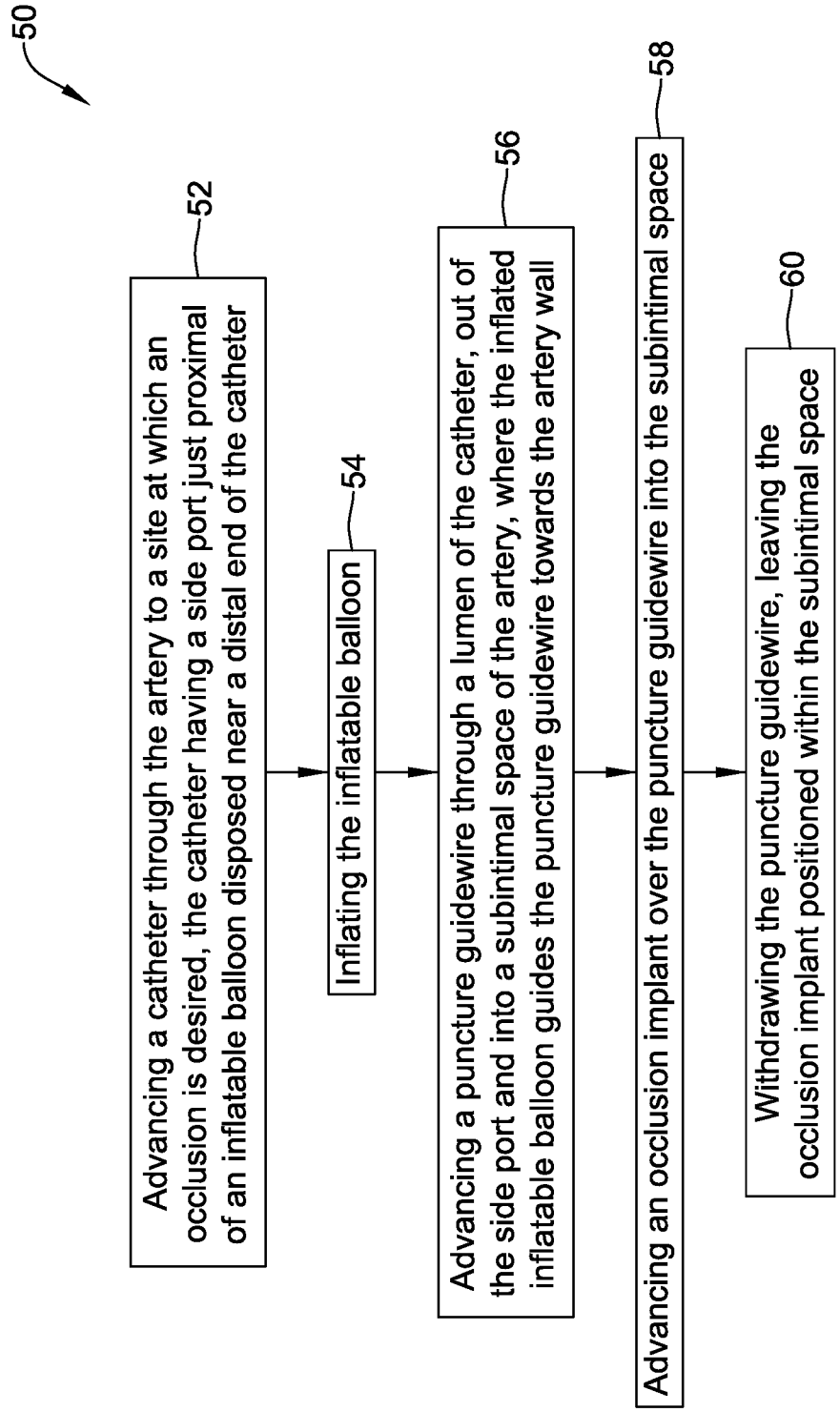
FIG. 5 is a flow diagram showing an illustrative method of occluding an artery using the illustrative catheter of FIG. 1.

FIG. 5 is a flow diagram showing an illustrative method 50 of occluding an artery, such as by using the catheter 10. A catheter is advanced through the artery to a site at which an occlusion is desired, the catheter having a side port just proximal of an inflatable balloon disposed near a distal end of the catheter, as indicated at block 52. The inflatable balloon is inflated, as indicated at block 54. A puncture guidewire is advanced through a lumen of the catheter, out of the side port and into a subintimal space of the artery, where the inflated inflatable balloon guides the puncture guidewire towards the artery wall, as indicated at block 56. An occlusion implant is advanced over the puncture guidewire into the subintimal space, as indicated at block 58. The puncture guidewire is withdrawn, leaving the occlusion implant positioned within the subintimal space, as indicated at block 60.

In some cases, the occlusion implant includes a hydrophilic material such as a hydrogel or a cross-linked gel. The occlusion implant may include a biosorbable material. The occlusion implant may include a rod-shaped profile and may include a lumen extending therethrough to allow the occlusion implant to be delivered over the puncture guidewire. The occlusion implant may have a distal end that is shaped to facilitate placement of the occlusion implant within a subintimal plane. The occlusion implant may have a proximal end that is relatively smaller, but this is not required in all cases. In some cases, the occlusion implant may have a central bulge, for example.

Figure 6:
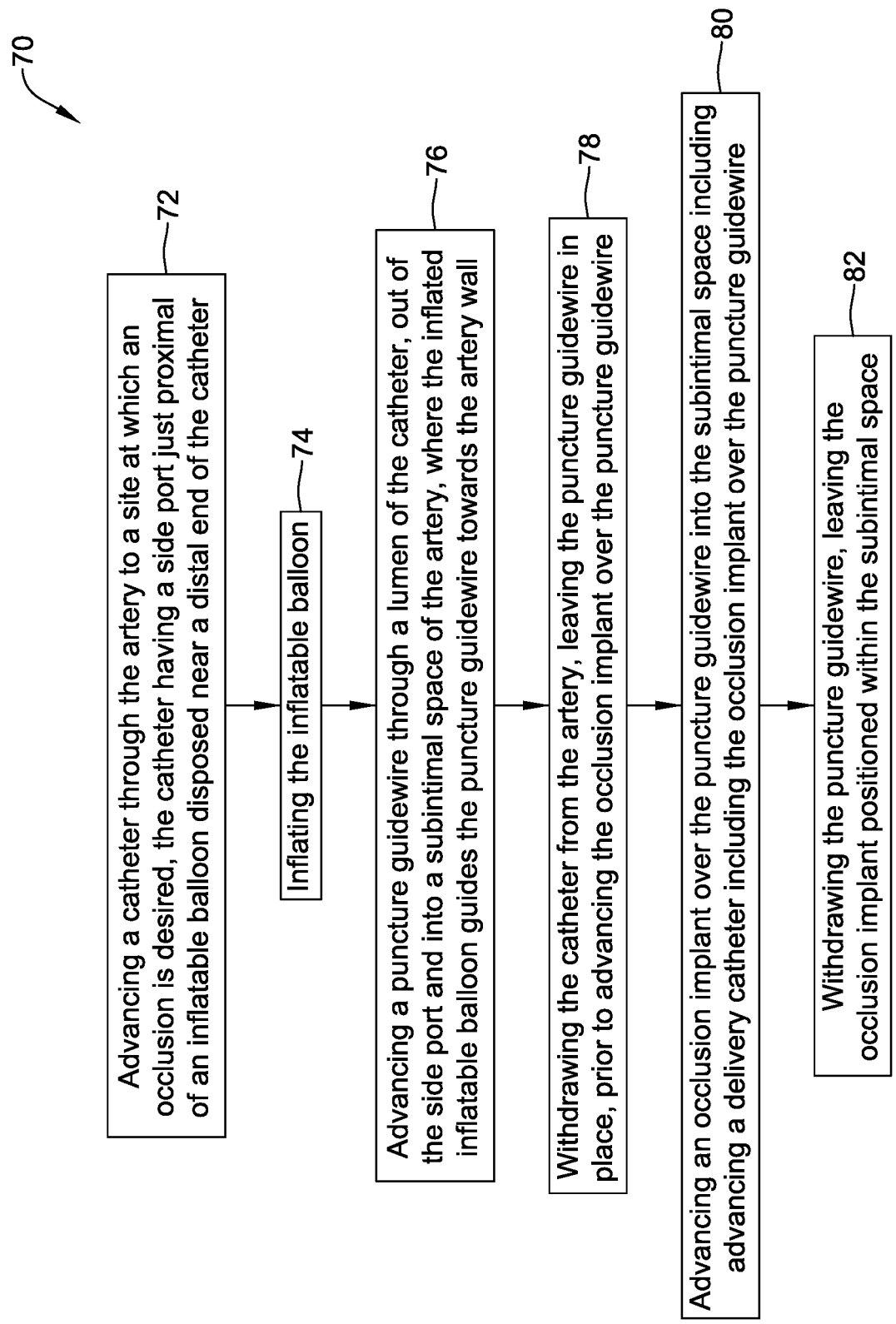
FIG. 6 is a flow diagram showing an illustrative method of occluding an artery using the illustrative catheter of FIG. 1.

FIG. 6 is a flow diagram showing an illustrative method 70 of occluding an artery, such as by using the catheter 10. A catheter is advanced through the artery to a site at which an occlusion is desired, the catheter having a side port just proximal of an inflatable balloon disposed near a distal end of the catheter, as indicated at block 72. The inflatable balloon is inflated, as indicated at block 74. A puncture guidewire is advanced through a lumen of the catheter, out of the side port and into a subintimal space of the artery, where the inflated inflatable balloon guides the puncture guidewire towards the artery wall, as indicated at block 76.

The catheter is withdrawn from the artery, leaving the puncture guidewire in place, prior to advancing the occlusion implant over the puncture guidewire, as indicated at block 78. An occlusion implant is advanced over the puncture guidewire into the subintimal space, including advancing a delivery catheter including the occlusion implant over the puncture guidewire, as indicated at block 80. The puncture guidewire is withdrawn, leaving the occlusion implant positioned within the subintimal space, as indicated at block 82.

Figure 7:
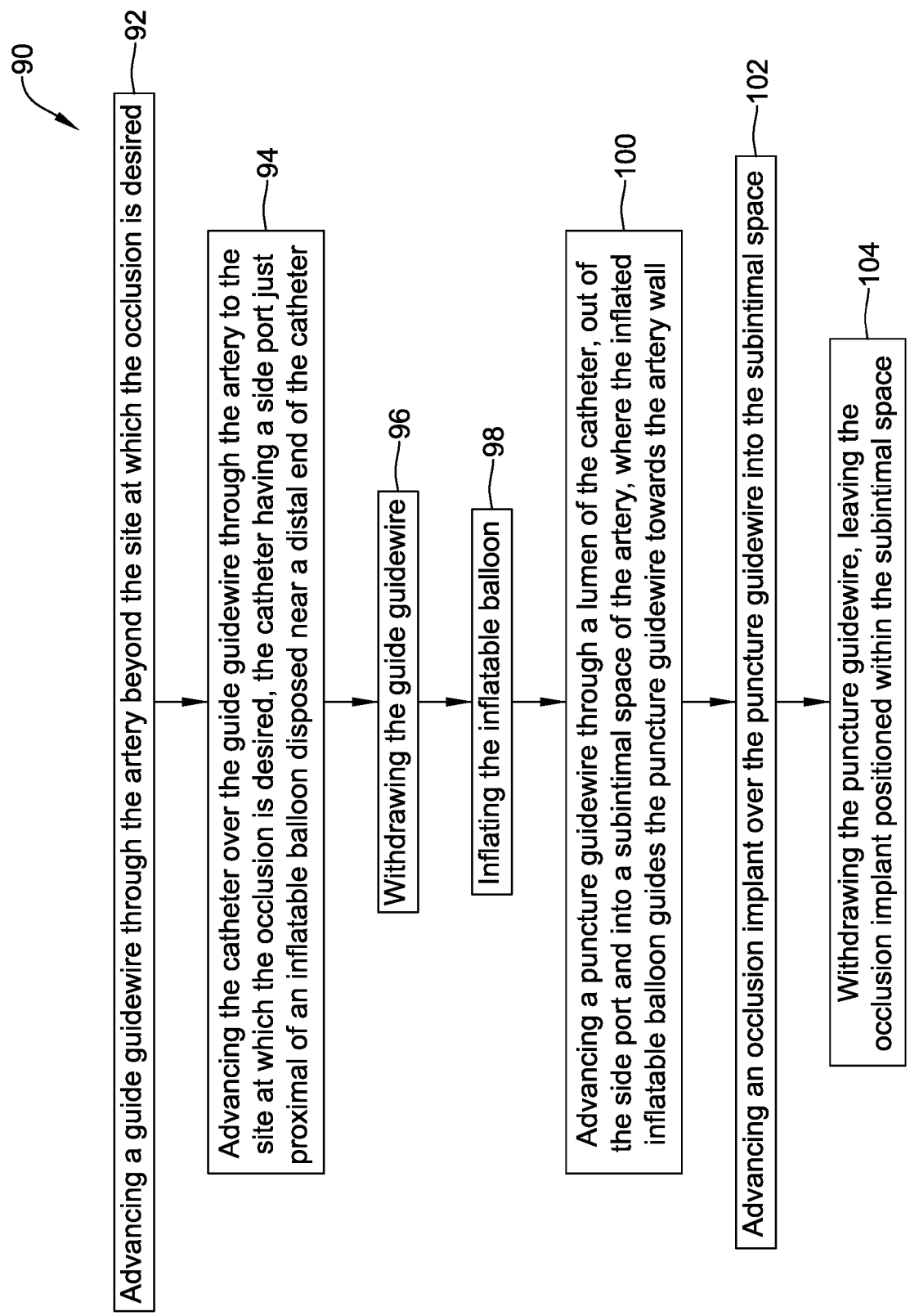
FIG. 7 is a flow diagram showing an illustrative method of occluding an artery using the illustrative catheter of FIG. 1.

FIG. 7 is a flow diagram showing an illustrative method 90 of occluding an artery, such as by using the catheter 10. A guide guidewire is advanced through the artery beyond the site at which the occlusion is desired, as indicated at block 92. The catheter is advanced over the guide guidewire through the artery to the site at which the occlusion is desired, the catheter having a side port just proximal of an inflatable balloon disposed near a distal end of the catheter, as indicated at block 94. The guide guidewire is withdrawn, as indicated at block 96. The inflatable balloon is inflated, as indicated at block 98. A puncture guidewire is advanced through a lumen of the catheter, out of the side port and into a subintimal space of the artery, where the inflated inflatable balloon guides the puncture guidewire towards the artery wall, as indicated at block 100.

An occlusion implant is advanced over the puncture guidewire into the subintimal space, including advancing a delivery catheter including the occlusion implant over the puncture guidewire, as indicated at block 102. The puncture guidewire is withdrawn, leaving the occlusion implant positioned within the subintimal space, as indicated at block 104.

Figure 8:
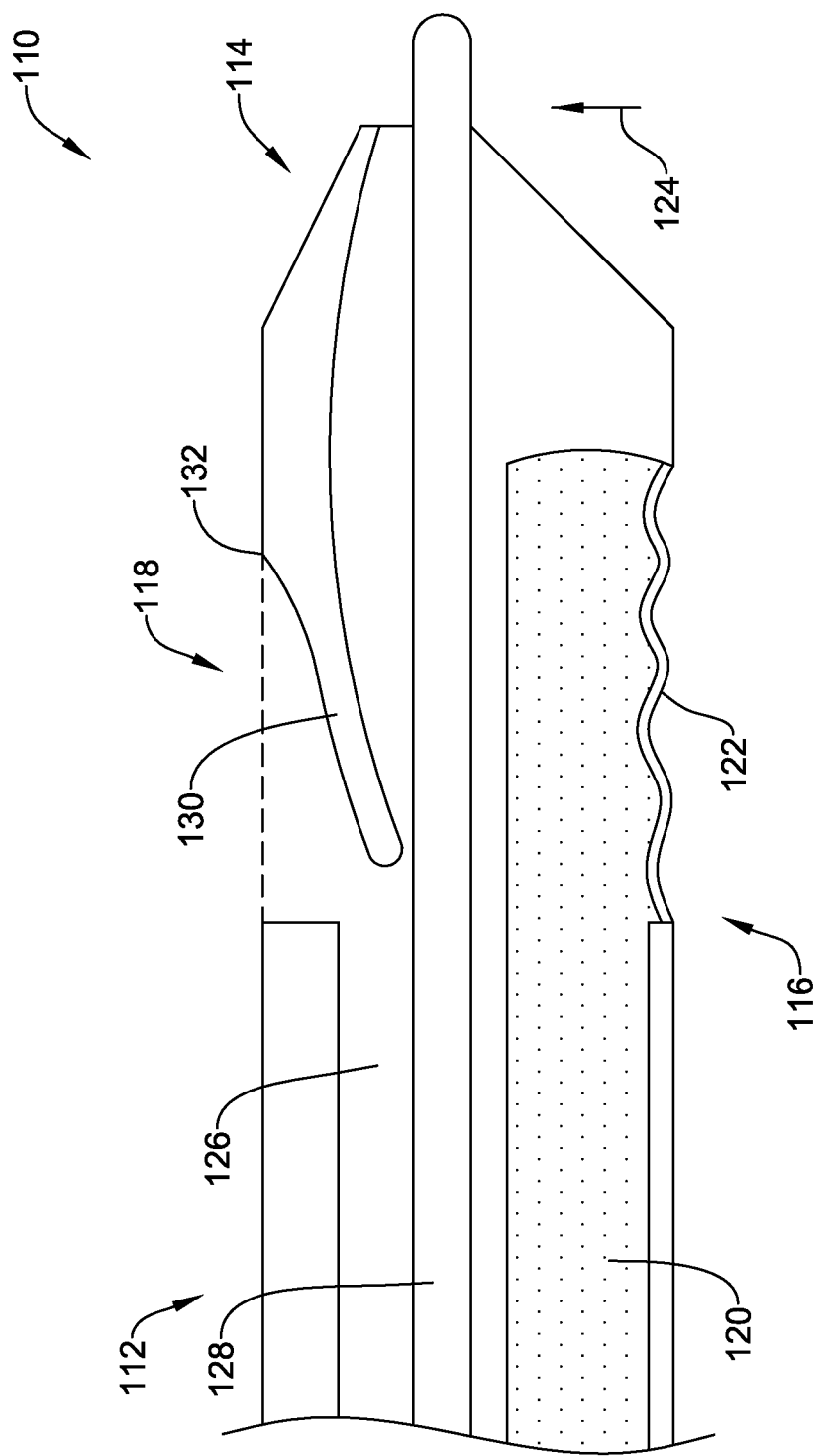
FIG. 8 is a schematic view of an illustrative catheter that is adapted for delivering an occlusion implant to a subintimal space within an artery wall.

FIG. 8 is a schematic view of an illustrative catheter 110 that is adapted for delivering an occlusion implant to a subintimal space within an artery wall. The illustrative catheter 110 includes an elongate shaft 112 having a distal region 114. The distal region 114 includes a first side 116 and a second side 118. It will be appreciated that in this, first and second are arbitrary, and are simply used to more easily reference how the catheter 110 will be used.

An inflation lumen 120 extends through the elongate shaft 112 and provides saline for inflating an inflatable balloon 122 that is fluidly coupled with the inflation lumen 120. The inflatable balloon 122 is disposed on the first side 116 of the distal region 114. It will be appreciated that inflating the inflatable balloon 122 can force the distal region 114 to move in a direction indicated by an arrow 124. A device lumen 126 extends through the elongate shaft 112. As shown in FIG. 8, a first guidewire 128 extends through the device lumen 126. In some cases, the first guidewire 128 is adapted to include an atraumatic tip.

A trap door 130 is disposed within the second side 118 of the distal region 114. In some cases, as shown, the trap door 130 is secured to the catheter 110 via a hinge 132 that is located at a distal end of the trap door 130. In some cases, the trap door 130 is adapted to pivot into the device lumen 126. As can be seen, the first guidewire 128 limits how far the trap door 130 can fall or pivot into the device lumen 126. It will be appreciated that the first guidewire 128 may be advanced through an artery to reach a site where an occlusion is desired, and the catheter 110 can then be advanced over the first guidewire 128 (with the first guidewire 128 extending through the device lumen 126 and the first guidewire 128 preventing the trap door 130 from falling or pivoting into the device lumen 126).

Figure 9:
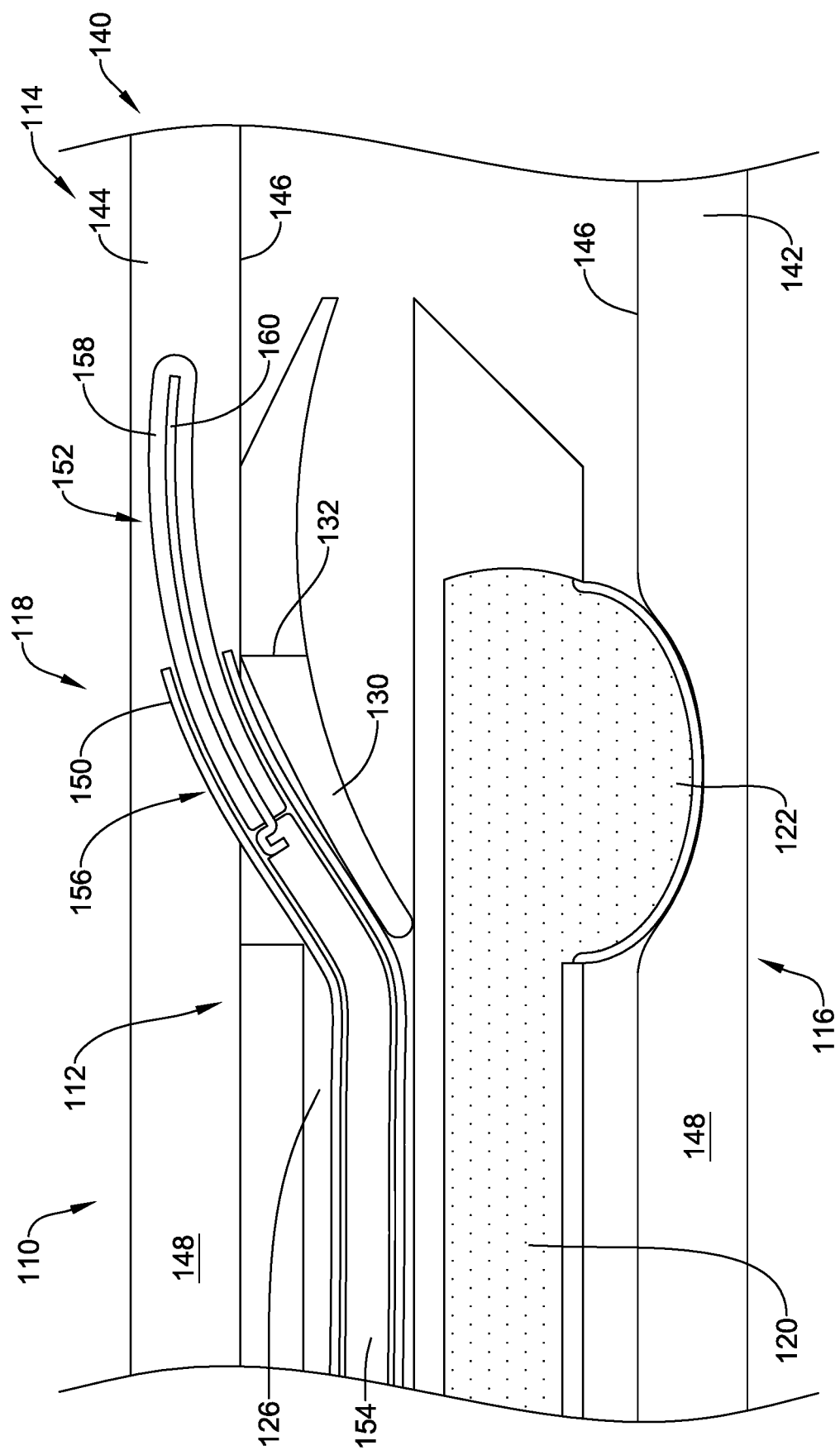
FIG. 9 is a schematic view of the illustrative catheter of FIG. 8, shown in position within an artery.

FIG. 9 is a schematic view of the illustrative catheter 110, shown in position within an artery 140. The artery 140 includes a first side 142 proximate the first side 116 of the catheter 110, and a second side 144 that is proximate the second side 118 of the catheter 110. The artery 140 includes an intima 146 and a subintimal space 148. As seen in FIG. 9, the inflatable balloon 120 has been inflated, thereby pushing the catheter 110 towards the second side 144 of the artery 140.

The first guidewire 128, shown in FIG. 8, has been withdrawn, which allows the trap door 130 to fall or pivot into the device lumen 126. While not shown here, a second guidewire having a tip that is adapted to puncture the intima 146 has been advanced through the device lumen 126, past the trap door 130, through the intima 146 and into the subintimal space 148. A second catheter 150 is advanced over the second guidewire before the second guidewire is withdrawn. With the second catheter 150 in position extending beyond the trap door 130 and into the subintimal space 148, an occlusion implant 152 that is coupled to an elongate member 154 for pushing the occlusion implant 152 into position extends through the second catheter 150. The occlusion implant 152 is coupled to the elongate member 154 via a coupling 156. In some cases, the elongate member 154 may include a stiffness transition from proximal to distal, in order to assist with navigating tortuous vasculature.

In some cases, the occlusion implant 152 includes a hydrogel or other hydrophilic coating 158 that is disposed about a central member 160. Once the occlusion implant 152 is disposed within the subintimal space 148, the coupling 156 can be disengaged and the elongate member 154 can be withdrawn through the second catheter 150. The second catheter 150 can subsequently be withdrawn from the device lumen 126, followed by withdrawing the catheter 110. Similarly to the occlusion implant 42, the occlusion implant 152 can absorb water from nearby blood plasma and can swell up, thereby forcing the intima 146 to at least partially close the artery 140.

In some cases, the occlusion implant 152 may be adapted to control the speed and degree of expansion by selecting the particular material and cross-linking density. In some cases, the occlusion implant 152 may be designed to permit sufficient time to deliver the occlusion implant 152 without significant expansion that could otherwise negatively impact delivery. The occlusion implant 152 may be designed so that once the occlusion implant 152 is implanted and exposed to fluid, it will expand fast enough to allow the operator to visualize and measure the amount of embolization. In some cases, the amount of pressure reduction may be measured as part of a procedure with a pressure wire, which is commonly used to measure FFR (fractional flow reserve) for cardiac stenting. Angiographically, using multiple planes, the cross-section of the artery post embolization can be visualized.

It will be appreciated that FIGS. 8 and 9 in combination show an illustrative assembly for providing an occlusion implant within the subintimal space of an artery. FIGS. 8 and 9 in combination show the catheter 110, the second catheter 150, the first guidewire 128, a second guidewire (not shown), an elongate member 154 for implanting the occlusion implant 152 as well as the occlusion implant 152 itself.

Figure 10:
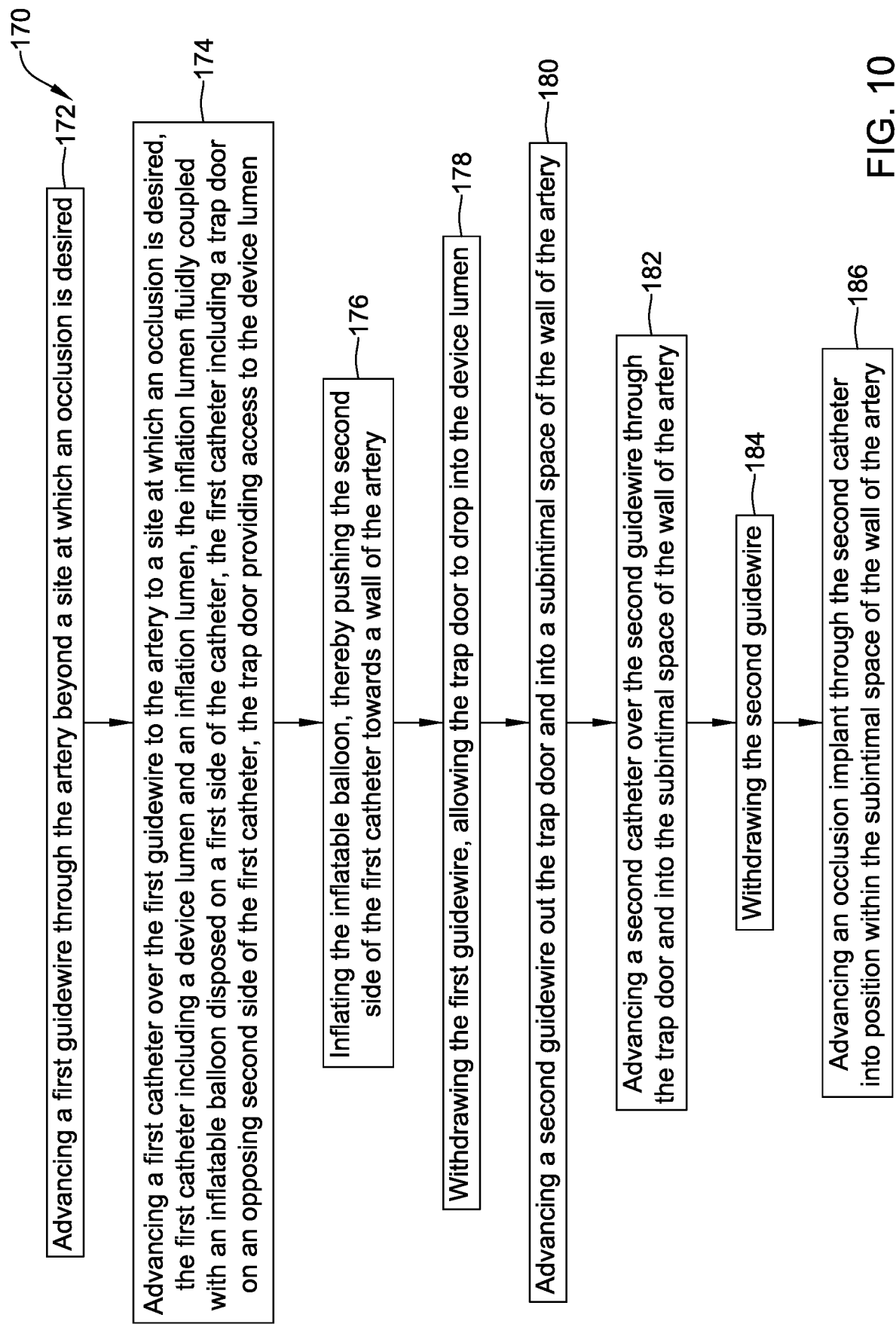
FIG. 10 is a flow diagram showing an illustrative method of occluding an artery using the illustrative catheter of FIG. 8.

FIG. 10 is a flow diagram showing an illustrative method 170 of occluding an artery using the illustrative catheter 110 of FIG. 8. A first guidewire is advanced through the artery beyond a site at which an occlusion is desired, as indicated at block 172. In some cases, the first guidewire includes an atraumatic tip. A first catheter is advanced over the first guidewire to the artery to a site at which an occlusion is desired, the first catheter including a device lumen and an inflation lumen, the inflation lumen fluidly coupled with an inflatable balloon disposed on a first side of the catheter, the first catheter including a trap door on an opposing second side of the first catheter, the trap door providing access to the device lumen, as indicated at block 174. The inflatable balloon is inflated, thereby pushing the second side of the first catheter towards a wall of the artery, as indicated at block 176.

The first guidewire is withdrawn, allowing the trap door to drop into the device lumen, as indicated at block 178. In some cases, the trap door is hinged to a sidewall of the first catheter via a hinge disposed on a distal end of the trap door. A second guidewire is advanced out the trap door and into a subintimal space of the wall of the artery, as indicated at block 180. In some cases, the second guidewire includes a tip that is adapted for piercing an intima of the artery wall. A second catheter is advanced over the second guidewire through the trap door and into the subintimal space of the wall of the artery, as indicated at block 182. The second guidewire is withdrawn, as indicated at block 184.

An occlusion implant is advanced through the second catheter into position within the subintimal space of the wall of the artery, as indicated at block 186. In some cases, advancing an occlusion implant through the second catheter into position within the subintimal space of the wall of the artery includes using an elongate member to push the occlusion implant through the second catheter. In some cases, the occlusion implant is adapted to temporarily occlude the artery. The occlusion implant may be adapted to permanently occlude the artery, for example.

Figure 11B:
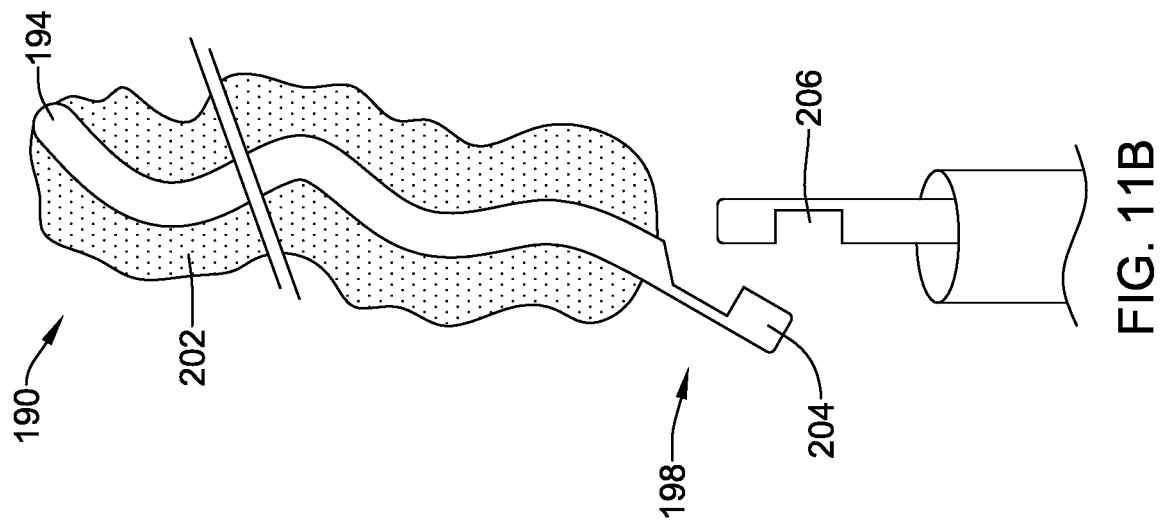
FIG. 11B is a schematic view of the illustrative occlusion implant of FIG. 11A, shown after implantation.
Figure 11A:
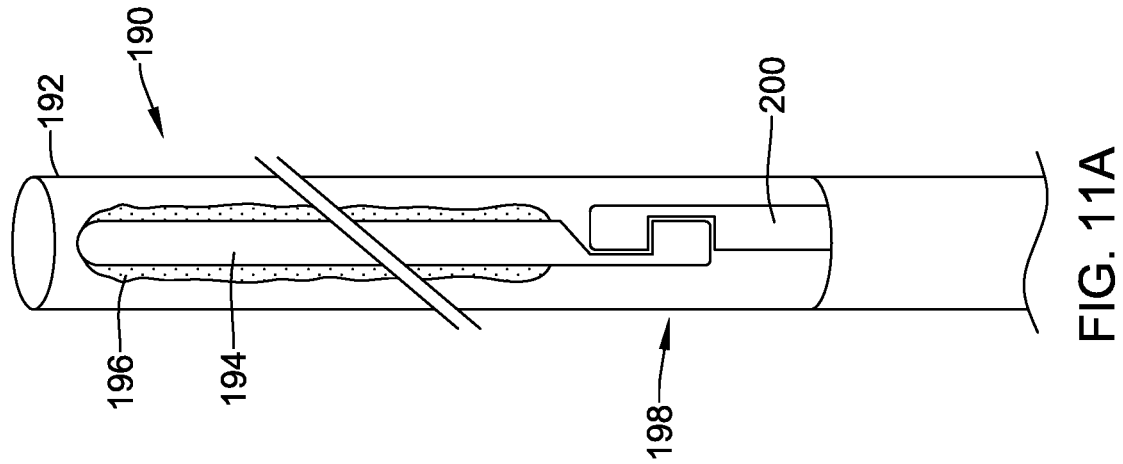
FIG. 11A is a schematic view of an illustrative occlusion implant prior to implantation.

FIG. 11A is a schematic view of an illustrative occlusion implant 192, shown within a catheter 192 prior to implantation. The occlusion implant 192 may be considered as being an example of the occlusion implant 152. The occlusion implant 192 includes an inner member 194 with a dry hydrogel 196 disposed on the inner member 194. In some cases, the inner member 194 may be a metallic core, although some polymers are also contemplated. As an example, the inner member 194 may have a diameter of about 0.018 inches and the dry hydrogel 196 may have a thickness of about 0.1 inches. Other dimensions are also contemplated. The inner member 194 extends proximally to a coupling mechanism 198 that releasably secures the occlusion implant 192 to a guidewire 200 for delivery.

FIG. 11B is a schematic view of the illustrative occlusion implant 192 of FIG. 11A, shown after implantation. As can be seen, the dry hydrogel 196 of FIG. 11A has now absorbed fluid and has swelled to become a hydrated hydrogel 202, which has grown to several times its dry diameter. In some cases, for example, the hydrated hydrogel 202 may have a thickness of about 0.75 inches, or about 7 or 8 times the thickness of the dry hydrogel 196. In some cases, the inner member 194 has a remembered configuration in which the inner member 194 regains a curved shape, as shown in FIG. 11B.

The coupling mechanism 198 includes a first tabbed member 204 that fits into a second tabbed member 206 that is secured to the guidewire 200. This is just an example, as other coupling mechanisms are contemplated. For example, the coupling mechanism 198 may include other mechanical or frictional securements. In some cases, the coupling mechanism 198 may include a magnetic coupling, for example.

Figure 12A:
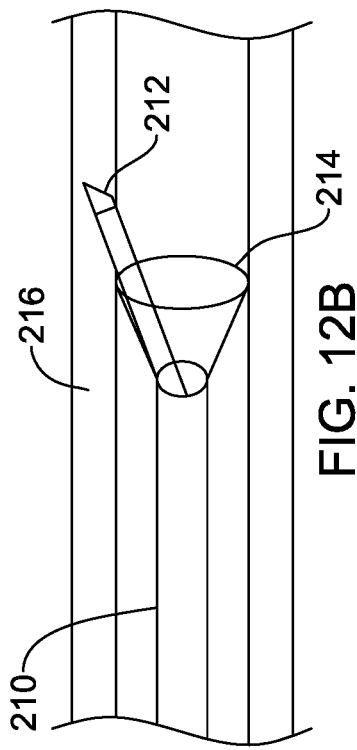
FIGS. 12A through 12D are schematic views showing implantation of an illustrative occlusion implant.
Figure 12B:
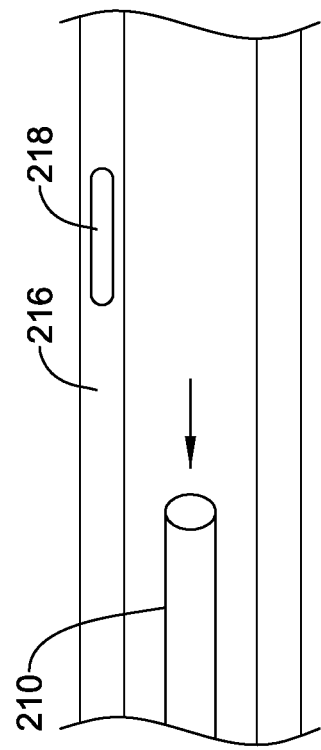
Figure 12C:
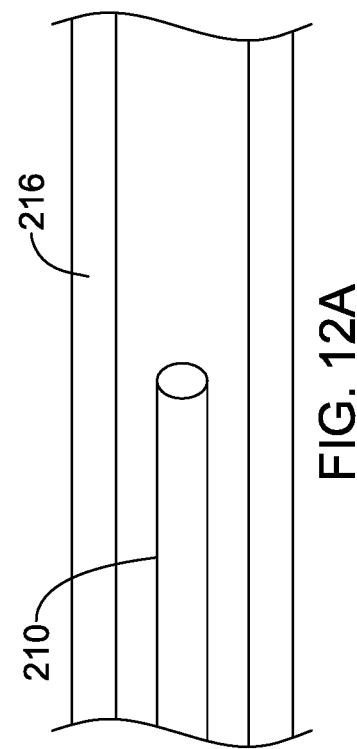
Figure 12D:
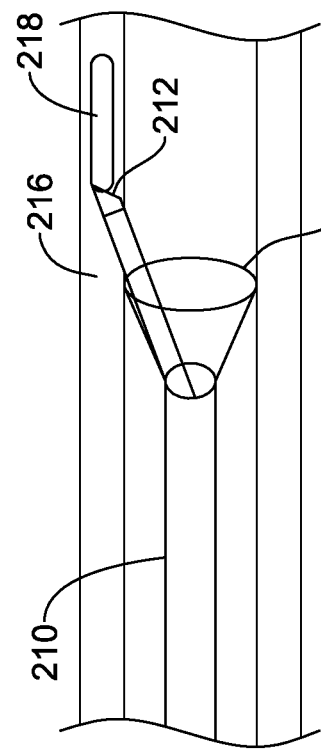

FIGS. 12A through 12D are schematic views showing implantation of an illustrative occlusion implant. In FIG. 12A, a primary catheter 210 holds a smaller, secondary cylinder 212, as shown in FIG. 12B. The primary catheter 210 includes a cone 214 that guides the secondary cylinder 212 towards a subintimal space 216. As seen in FIG. 12C, an occlusion implant 218 has been advanced out of the secondary cylinder 212 and into the subintimal space 216. As shown in FIG. 12D, the occlusion implant 218 remains within the subintimal space 216 while the primary catheter 210 is being withdrawn.

FIG. 13A through 13C are schematic views showing an illustrative catheter 220 useful in implanting an occlusion implant. The catheter 220 is shown disposed within an example artery 222 including a subintimal space 224. The catheter 220 includes a guidewire lumen 226 extending through the catheter 220. The catheter 220 includes a series of cutouts 228 that enable a distal region 230 to curve back on itself, thereby providing an opportunity to gain access to the subintimal space 224 in a direction opposite the direction in which the catheter 220 is advanced within the artery 222. A wire 232 extends between the distal region 230 of the catheter 220 and a mechanism 234 that can be used to increase or decrease the tension applied to the distal region 230 of the catheter 220. By increasing the tension, for example, one can cause the distal region 230 of the catheter 220 to bend back on itself, as seen in FIGS. 13B and 13C.

With particular reference to FIG. 13C, an implant guidewire 236 can be advanced distally through the catheter 220 and into the subintimal space 224 once the distal region 230 has been bent back on itself. At this point, any desired occlusion implant, such as the occlusion implant 42, the occlusion implant 152 or the occlusion implant 190 may be advanced over the implant guidewire 236 and thus reach the subintimal space 224 and be implanted within the subintimal space 224.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of occluding an artery, comprising:
   advancing a catheter through the artery to a site at which an occlusion is desired, the catheter having a side port just proximal of an inflatable balloon disposed near a distal end of the catheter;
   inflating the inflatable balloon;
   advancing a puncture guidewire through a lumen of the catheter, out of the side port and into a subintimal space of the artery, where the inflated inflatable balloon guides the puncture guidewire towards a wall of the artery;
   advancing an occlusion implant over the puncture guidewire into the subintimal space; and
   withdrawing the puncture guidewire, leaving the occlusion implant positioned within the subintimal space.

2. The method of claim 1, further comprising withdrawing the catheter from the artery, leaving the puncture guidewire in place, prior to advancing the occlusion implant over the puncture guidewire.

3. The method of claim 2, wherein advancing the occlusion implant over the puncture guidewire further comprises advancing a delivery catheter including the occlusion implant over the puncture guidewire.

4. The method of claim 1, wherein the catheter further comprises a central guidewire lumen, and advancing the catheter through the artery comprises:

advancing a guide guidewire through the artery beyond the site at which the occlusion is desired; and advancing the catheter over the guide guidewire through the artery to the site at which the occlusion is desired.

5. The method of claim 4, further comprising withdrawing the guide guidewire.

6. The method of claim 1, wherein the occlusion implant comprises a hydrophilic material.

7. The method of claim 1, wherein the occlusion implant comprises a biosorbable material.

8. The method of claim 1, wherein the occlusion implant comprises a rod-shaped profile and includes a lumen extending therethrough to allow the occlusion implant to be delivered over the puncture guidewire.

9. A method of occluding an artery, comprising:

advancing a first guidewire through the artery beyond a site at which an occlusion is desired;

advancing a first catheter over the first guidewire to the artery to the site at which an occlusion is desired, the first catheter including a device lumen and an inflation lumen, the inflation lumen fluidly coupled with an inflatable balloon disposed on a first side of the first catheter, the first catheter including a trap door on an opposing second side of the first catheter, the trap door providing access to the device lumen;

inflating the inflatable balloon, thereby pushing the second side of the first catheter towards a wall of the artery;

withdrawing the first guidewire, allowing the trap door to drop into the device lumen;

advancing a second guidewire out the trap door and into a subintimal space of the wall of the artery;

advancing a second catheter over the second guidewire through the trap door and into the subintimal space of the wall of the artery;

withdrawing the second guidewire; and advancing an occlusion implant through the second catheter into position within the subintimal space of the wall of the artery;

wherein the occlusion implant is adapted to permanently occlude the artery.

10. The method of claim 9, wherein the first guidewire includes an atraumatic tip.

11. The method of claim 9, wherein the second guidewire includes a tip adapted for piercing an intima of a wall of the artery.

12. The method of claim 9, wherein the trap door is hinged to a sidewall of the first catheter via a hinge disposed on a distal end of the trap door.

13. The method of claim 9, wherein advancing the occlusion implant through the second catheter into position within the subintimal space of the wall of the artery comprises using an elongate member to push the occlusion implant through the second catheter.

\* \* \* \* \*